US007514218B2

(12) United States Patent
Blanche et al.

(10) Patent No.: US 7,514,218 B2
(45) Date of Patent: *Apr. 7, 2009

(54) PROCESSES FOR PURIFYING AND FOR DETECTING TARGET DOUBLE-STRANDED DNA SEQUENCES BY TRIPLE HELIX INTERACTION

(75) Inventors: Francis Blanche, Paris (FR); Beatrice Cameron, Paris (FR)

(73) Assignee: Centelion (FR)

( * ) Notice: Subject to any disclaimer, the term of this patent is extended or adjusted under 35 U.S.C. 154(b) by 313 days.

This patent is subject to a terminal disclaimer.

(21) Appl. No.: 11/378,356

(22) Filed: Mar. 20, 2006

(65) Prior Publication Data

US 2006/0205000 A1 Sep. 14, 2006
US 2008/0064031 A9 Mar. 13, 2008

Related U.S. Application Data

(62) Division of application No. 10/104,025, filed on Mar. 25, 2002, now Pat. No. 7,052,838.

(60) Provisional application No. 60/285,272, filed on Apr. 23, 2001.

(30) Foreign Application Priority Data

Mar. 23, 2001 (FR) .................................. 01 03953

(51) Int. Cl.
*C12Q 1/68* (2006.01)
*C12P 19/34* (2006.01)
*C07H 21/04* (2006.01)
(52) U.S. Cl. ........................... 435/6; 435/91.2; 536/23.1
(58) Field of Classification Search ....................... None
See application file for complete search history.

(56) References Cited

U.S. PATENT DOCUMENTS

| 6,265,166 | B1 | 7/2001 | Frank-Kamenetskii et al. | |
| 6,287,762 | B1 | 9/2001 | Crouzet et al. | |
| 6,319,672 | B1 * | 11/2001 | Crouzet et al. | 435/6 |
| 6,977,174 | B2 | 12/2005 | Crouzet et al. | |
| 7,279,313 | B2 | 10/2007 | Soubrier | |
| 7,364,894 | B2 | 4/2008 | Soubrier | |

FOREIGN PATENT DOCUMENTS

| WO | WO 96/18744 | 6/1996 |
| WO | WO 00/46366 | 8/2000 |
| WO | WO 2004/108167 | 12/2004 |

OTHER PUBLICATIONS

Bukanov et al., Proc. Natl. Acad. Sci. USA, 95:5516-5520 (1998).
Fossella, J.A., et al., "Relative Specificities in Binding of Watson—Crick Base Pairs by Third Strand Residues in a DNA Pyrimidine Triplex Motif," *Nucleic Acids Research*, 21:4511-4515 (1993).
Gowers, D.M. and Fox, K.R., "Triple Helix Formation at $(AT)_n$ Adjacent to an Oligopurine Tract," *Nucleic Acids Research*, 26:3626-3633 (1998).
Gowers, D.M., et al., "DNA Triple Helix Formation at Oligopurine Sites Containing Multiple Contiguous Pyrimidines," *Nucleic Acids Research*, 25:3787-3794 (1997).
Kiessling L.L., et al. "Flanking Sequence Effects Within the Pyrimidine Triple-Helix Motif Characterized by Affinity Cleaving," *Biochemistry*, 31:2829-2834 (1992).
Radhakrishnan, I., et al. "DNA Triplexes: Solution Structures, Hydration Sites, Energetics, Interactions, and Function," *Biochemistry*, 33:11405-11416 (1994).
Soyfer, V.N. and Potaman, V.N., eds., "Triple-Helical Nucleic Acids,"Chapter 4: Triplex Recognition pp. 151-169, Springer, (1995).
Takabatake et al., Nucleic Acids Research, 20:5853-5854 (1992).
Yoon, K., et al., "Elucidation of the Sequence-Specific Third-Strand Recognition of Four Watson—Crick Base Pairs in a Pyrimidine Triple-Helix Motif: T•AT, C•GC, T•CG, and G•TA," *Proc. Natl. Acad. Sci. USA.*, 89:3840-3844 (1992).
Carrière et al., "Optimization of plasmids for gene delivery," STP PHARMA Sciences, 2001, vol. 11 No. 1, pp. 5-10.
Presentation entitled "Gene Therapy for Ischemic Disease," by Beatrice Cameron, Sep. 23-27, 1998, Cold Spring Harbor Laboratory, New York.
Presentation entitled "FGF-1 Gene Delivery: Preliminary Clinical Results in Peripheral Vascular Disease," by Richard Pilsudski, Third Annual Angiogenesis Mini-Summit, New Orleans, La., Nov. 11, 2000.
Presentation entitled Arteriopathie des Membres Inferieurs: Quoi de neuf 2001 Therapie Genique, by Richard Pilsudski, Journees Internationales d'Angeiologie, Paris, Jan. 12-13, 2001.
Presentation entitled "Strategies for Clinical Application of Angiogenesis-Myogenesis Research," by Richard Pilsudski, 7th Local Drug Delivery Meeting and Cardiovascular Course on Radiation and Molecular Strategies, Geneva, Switzerland, Jan. 25-27, 2001.
Presentation entitled Angiogenesis: Promoting Angiogenesis: Angiogenesis Gene Therapy for Peripheral Vascular Disease, by Richard Pilsudski, Institut Pasteur Euroconferences, Paris, Mar. 8-9, 2001.

(Continued)

*Primary Examiner*—Gary Benzion
*Assistant Examiner*—Cynthia B Wilder
(74) *Attorney, Agent, or Firm*—Finnegan, Henderson, Farabow, Garrett & Dunner, LLP

(57) ABSTRACT

The present invention relates to novel target double-stranded DNA sequences capable of interacting with a third strand and of forming a stable triple helix. The present invention also relates to a process for purifying a double-stranded DNA molecule, according to which a solution containing said DNA molecule is brought into contact with a third DNA strand capable of forming, by hybridization, a triple helix structure with a target double-stranded DNA sequence carried by said DNA molecule.

17 Claims, 9 Drawing Sheets

OTHER PUBLICATIONS

Figure 1:
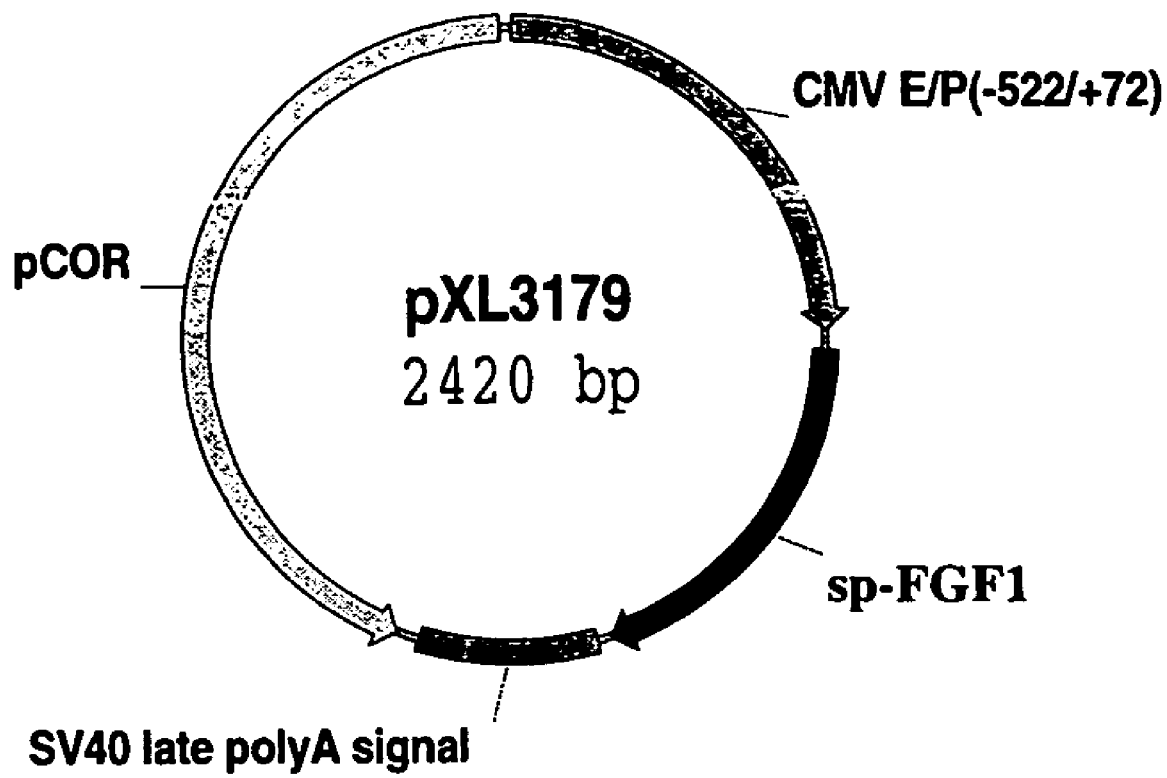

Presentation entitled "Large-Scale Purification of Plasmid DNA b Triplex Affinity Chromotography," by Francis Blanche, Recovery X, Cancun, Jun. 3-8, 2001.

Presentation entitled "Therapeutic Angiogenesis in Peripheral Vascular Disease—Final Results of the Phase I Trial on FGF-1 Gene Delivery," by Richard Pilsudski, Angiogenesis & DMR, Washington., Jun. 21-22, 2001.

Presentation entitled Purification of Plasmid DNA by Triplex Affinity Chromotography, by Francis Blanche, Downstream Processing of Nucleic Acids, Sep. 17-18, 2001.

Presentation entitled Therapeutische Angiogenese: Clinical Results of NV1FGF Gene Therapy in Chronic Limb Ischemia, by Richard Pilsudski, Angio 2001, Nov. 29-Dec. 1, 2001, Bern.

Presentation entitled "pCOR Gene Therapy Plasmid: Improvements of Existing Technology," by Fabienne Soubrier, ESGT, approximate date Oct. 13, 2002.

Presentation entitled "Final Results of a FGF-1 Gene Therapy Clincial Trial in Patients with Critical Limb Ischemia," by Marie-Helene Francois, 17$^{th}$ International Congress on Thrombosis, Oct. 30, 2002, Bologna, Italy.

Presentation entitled A Phage 1 Study to Evaluate the Safety and Biological Activity of Plasmid DNA Encoding FGF1 in Patients with Severe Peripheral Artery Occlusive Disease, by Michael Coleman, Angiogenesis: Gene Therapy of Cardiovascular Diseases with Angiogenic Growth Factors, SMI, Feb. 17-18, 2003, The Hatton, London.

Presentation entitled "Quality Control of NV1FGF Plasmid DNA for PAD Gene Therapy," by Didier Faucher, International Symposium organized by EDQM on Standardization and Quality Control Cell and Gene Therapy Products, EDQM meeting, Feb. 24-25, 2003, Strasbourg.

Faucher et al., "Quality Control of NV1FGF Plasmid DNA for PAD Gene Therapy," Standardization & QC Cell and Gene Therapy Products, for meeting held Feb. 24-25, 2003, Strasbourg, France.

Talisman™ Brochure, American Heart Association, approximate date Nov. 3, 2003.

Presentation entitled "Large-Scale Production of Plasmids for Gene Therapy," by Francis Blanche, SMBC, Singapore, Apr. 20, 2004.

Presentation entitled, Treatment of Peripheral Arterial Disease with NV1FGF, Tlaisman™ Trials, by Michael Coleman, ,SMI, May 17-18, The Hatton, London.

Presentation entitled Talisman 105™: IM Injections of NV1FGF in CLI Patients with Planned Amputation, by Iris Baumgartner, American Heart Association, Nov. 8, 2004.

Presentation entitled Gene Therapy for the Treatment of Peripheral Arterial Disease, by Francois Meyer, ESGT, Oct. 28, 2005.

Presentation entitled "Therapeutic Angiogenesis with Intramuscular NV1FGF Improves Amputation-Free Survival in Patients with Critical Limb Ischemia," by S. Nikol et al., ACC.06 i2 Summit 2006, Mar. 11-14, Atlanta.

* cited by examiner

Mutagenic and sequential PCR
between the sites Eco47III and NsiI

SEQUENCE LISTING

<160> NUMBER OF SEQ ID NOS: 33

<210> SEQ ID NO 1
<211> LENGTH: 20
<212> TYPE: DNA
<213> ORGANISM: Homo sapiens

<400> SEQUENCE: 1
aagaagcatg cagagaagaa                                                     20

<210> SEQ ID NO 2
<211> LENGTH: 20
<212> TYPE: DNA
<213> ORGANISM: Artificial
<220> FEATURE:
<223> OTHER INFORMATION: Oligonucleotide

<400> SEQUENCE: 2
ttcttcttct tcttcttctt                                                     20

<210> SEQ ID NO 3
<211> LENGTH: 20
<212> TYPE: DNA
<213> ORGANISM: Artificial
<220> FEATURE:
<223> OTHER INFORMATION: Oligonucleotide

<400> SEQUENCE: 3
ttcttcttgc ttctcttctt                                                     20

<210> SEQ ID NO 4
<211> LENGTH: 20
<212> TYPE: DNA
<213> ORGANISM: Artificial
<220> FEATURE:
<223> OTHER INFORMATION: Oligonucleotide

<400> SEQUENCE: 4
ttcttcttgt ttctcttctt                                                     20

<210> SEQ ID NO 5
<211> LENGTH: 20
<212> TYPE: DNA
<213> ORGANISM: Artificial
<220> FEATURE:
<223> OTHER INFORMATION: Oligonucleotide

<400> SEQUENCE: 5
ttcttcttcc ttctcttctt                                                     20

<210> SEQ ID NO 6

```
<211> LENGTH: 16
<212> TYPE: DNA
<213> ORGANISM: Homo sapiens

<400> SEQUENCE: 6
gaagaagcac gagaag                                                      16

<210> SEQ ID NO 7
<211> LENGTH: 16
<212> TYPE: DNA
<213> ORGANISM: Homo sapiens

<400> SEQUENCE: 7
aaagaaagca gggaag                                                      16

<210> SEQ ID NO 8
<211> LENGTH: 13
<212> TYPE: DNA
<213> ORGANISM: Homo sapiens

<400> SEQUENCE: 8
gaagaggaag aag                                                         13

<210> SEQ ID NO 9
<211> LENGTH: 14
<212> TYPE: DNA
<213> ORGANISM: Homo sapiens

<400> SEQUENCE: 9
aaggagaaga agaa                                                        14

<210> SEQ ID NO 10
<211> LENGTH: 15
<212> TYPE: DNA
<213> ORGANISM: Homo sapiens

<400> SEQUENCE: 10
aagatgagga agaag                                                       15

<210> SEQ ID NO 11
<211> LENGTH: 25
<212> TYPE: DNA
<213> ORGANISM: Artificial
<220> FEATURE:
<223> OTHER INFORMATION: Oligonucleotide

<400> SEQUENCE: 11
gaggcttctt cttcttcttc ttctt                                            25

<210> SEQ ID NO 12
<211> LENGTH: 13
<212> TYPE: DNA
<213> ORGANISM: Artificial
<220> FEATURE:
<223> OTHER INFORMATION: Oligonucleotide

<400> SEQUENCE: 12
ccttttcctc ctt                                                         13

<210> SEQ ID NO 13
<211> LENGTH: 13
<212> TYPE: DNA
<213> ORGANISM: Artificial
<220> FEATURE:
<223> OTHER INFORMATION: Oligonucleotide
```

-continued

<400> SEQUENCE: 13
ggcaacggag gaa                                                              13

<210> SEQ ID NO 14
<211> LENGTH: 11
<212> TYPE: DNA
<213> ORGANISM: Artificial
<220> FEATURE:
<223> OTHER INFORMATION: Oligonucleotide

<400> SEQUENCE: 14
tcctctccct c                                                                11

<210> SEQ ID NO 15
<211> LENGTH: 11
<212> TYPE: DNA
<213> ORGANISM: Homo sapiens

<400> SEQUENCE: 15
aggagcggga g                                                                11

<210> SEQ ID NO 16
<211> LENGTH: 13
<212> TYPE: DNA
<213> ORGANISM: Artificial
<220> FEATURE:
<223> OTHER INFORMATION: Oligonucleotide

<400> SEQUENCE: 16
tttcctctcc ctc                                                              13

<210> SEQ ID NO 17
<211> LENGTH: 28
<212> TYPE: DNA
<213> ORGANISM: Artificial
<220> FEATURE:
<223> OTHER INFORMATION: Oligonucleotide

<400> SEQUENCE: 17
gatccaagaa gcatgcagag aagaattc                                              28

<210> SEQ ID NO 18
<211> LENGTH: 21
<212> TYPE: DNA
<213> ORGANISM: Artificial
<220> FEATURE:
<223> OTHER INFORMATION: Oligonucleotide

<400> SEQUENCE: 18
gaagaaggga aagaagatct g                                                     21

<210> SEQ ID NO 19
<211> LENGTH: 21
<212> TYPE: DNA
<213> ORGANISM: Artificial
<220> FEATURE:
<223> OTHER INFORMATION: Oligonucleotide

<400> SEQUENCE: 19
gaagaaagga gagaagatct g                                                     21

<210> SEQ ID NO 20
<211> LENGTH: 21
<212> TYPE: DNA

```
<213> ORGANISM: Artificial
<220> FEATURE:
<223> OTHER INFORMATION: Oligonucleotide

<400> SEQUENCE: 20
gaagaagttt aagaagatct g                                              21

<210> SEQ ID NO 21
<211> LENGTH: 4
<212> TYPE: DNA
<213> ORGANISM: Artificial
<220> FEATURE:
<223> OTHER INFORMATION: Oligonucleotide

<400> SEQUENCE: 21 gagg                                                                  4

<210> SEQ ID NO 22
<211> LENGTH: 7
<212> TYPE: DNA
<213> ORGANISM: Artificial
<220> FEATURE:
<223> OTHER INFORMATION: Oligonucleotide

<400> SEQUENCE: 22 agaagaa                                                               7

<210> SEQ ID NO 23
<211> LENGTH: 6
<212> TYPE: DNA
<213> ORGANISM: Artificial
<220> FEATURE:
<223> OTHER INFORMATION: Oligonucleotide

<400> SEQUENCE: 23 aagaag                                                                6

<210> SEQ ID NO 24
<211> LENGTH: 13
<212> TYPE: DNA
<213> ORGANISM: Artificial
<220> FEATURE:
<223> OTHER INFORMATION: Oligonucleotide

<400> SEQUENCE: 24
aagaagcatg cag                                                       13

<210> SEQ ID NO 25
<211> LENGTH: 13
<212> TYPE: DNA
<213> ORGANISM: Artificial
<220> FEATURE:
<223> OTHER INFORMATION: Oligonucleotide

<400> SEQUENCE: 25
atgcagagaa gaa                                                       13

<210> SEQ ID NO 26
<211> LENGTH: 17
<212> TYPE: DNA
<213> ORGANISM: Artificial
<220> FEATURE:
<223> OTHER INFORMATION: Oligonucleotide

<400> SEQUENCE: 26
cttcttcttc ttcttct                                                   17
```

```
<210> SEQ ID NO 27
<211> LENGTH: 17
<212> TYPE: DNA
<213> ORGANISM: Artificial
<220> FEATURE:
<223> OTHER INFORMATION: Oligonucleotide

<400> SEQUENCE: 27
gaagaaggga aagaaga                                                    17

<210> SEQ ID NO 28
<211> LENGTH: 17
<212> TYPE: DNA
<213> ORGANISM: Artificial
<220> FEATURE:
<223> OTHER INFORMATION: Oligonucleotide

<400> SEQUENCE: 28
gaagaaagga gagaaga                                                    17

<210> SEQ ID NO 29
<211> LENGTH: 17
<212> TYPE: DNA
<213> ORGANISM: Artificial
<220> FEATURE:
<223> OTHER INFORMATION: Oligonucleotide

<400> SEQUENCE: 29
gaagaagttt aagaaga                                                    17

<210> SEQ ID NO 30
<211> LENGTH: 7
<212> TYPE: DNA
<213> ORGANISM: Artificial
<220> FEATURE:
<223> OTHER INFORMATION: Oligonucleotide

<400> SEQUENCE: 30 cctcctt                                                                7

<210> SEQ ID NO 31
<211> LENGTH: 7
<212> TYPE: DNA
<213> ORGANISM: Homo sapiens

<400> SEQUENCE: 31 ggaggaa                                                                7

<210> SEQ ID NO 32
<211> LENGTH: 11
<212> TYPE: DNA
<213> ORGANISM: Artificial
<220> FEATURE:
<223> OTHER INFORMATION: Oligonucleotide

<400> SEQUENCE: 32 tttttttttcc t                                                         11

<210> SEQ ID NO 33
<211> LENGTH: 11
<212> TYPE: DNA
<213> ORGANISM: Homo sapiens
```

```
<400> SEQUENCE: 33
aaaaaaaagg a                                                                                              11
```

PROCESSES FOR PURIFYING AND FOR DETECTING TARGET DOUBLE-STRANDED DNA SEQUENCES BY TRIPLE HELIX INTERACTION

This is a division of application Ser. No. 10/104,025, filed Mar. 25, 2002, now U.S. Pat. No. 7,052,838, which claims the benefit of U.S. Provisional Application No. 60/285,272, filed Apr. 23, 2001, the content of which are incorporated herein by reference, and claims the right to priority based on French Patent Application No. 0103953, filed Mar. 23, 2001.

The present invention relates to novel target DNA sequences capable of forming structures of the triple helix type, and also to a novel process for purifying DNA. More particularly, the purification process according to the invention implements hybridization between a target DNA sequence and an oligonucleotide. The process according to the invention proves to be particularly useful since it makes it possible to purify double-stranded DNA of pharmaceutical quality with high yields.

The present invention also relates to novel methods for detecting, for quantifying, for isolating or for sorting DNA molecules containing said specific target sequences.

The purification processes according to the invention are essentially based on triple helix interaction between a particular target DNA sequence and an oligonucleotide composed of natural or modified bases.

It has been shown that homopyrimidine oligonucleotides are capable of interacting specifically in the major groove of the DNA double helix so as to locally form three-stranded structures named triple helices (Moser et al., *Science* 238 (1987) 645; Povsiz et al., *J. Am. Chem.* 111 (1989) 3059). These oligonucleotides selectively recognize the DNA double helix at oligopurine-oligopyrimidine sequences, i.e. at regions having an oligopurine sequence on one strand and an oligopyrimidine sequence on the complementary strand, and form a triple helix locally there. The bases of the homopyrimidine oligonucleotide third strand form hydrogen bonds (Hoogsteen-type bonds) with the purines of the Watson-Crick base pairs.

Similarly, structures of the triple helix type can form between a homopurine oligonucleotide and a homopurine-homopyrimidine double-stranded DNA. In this type of structure, the purine bases of the oligonucleotide form reverse Hoogsteen-type bonds with the purine bases of the double-stranded DNA.

These site-specific triple helix interactions have in particular been used by Looney et al. (*Science* 241 (1988) 456) for controlling the expression of certain genes, and by Hélène et al. (*BBA* 1049 (1990) 99; WO 95/18223) who describe the formation of triple helix structures between oligonucleotides and target sequences present in promoters or coding regions, and thus the possibility of modulating the expression profile of these genes, probably via inhibitory action of RNA polymerase at the level of initiation and/or elongation.

This type of triple helix interaction, for purifying plasmid DNA from a complex mixture which contains the DNA molecule mixed with other components, has also been described in international application WO 96/18744 for purifying plasmid DNA. More particularly, that application describes a process for purifying double-stranded DNA, consisting in bringing the complex mixture into contact with a support to which an oligonucleotide capable of forming, by hybridization, a triple helix with a specific sequence of the target DNA is covalently coupled.

In this specific interaction of the triple helix type for purification purposes, the specificity is due to pairings involving hydrogen bonds of the Hoogsteen type between, firstly, thymine (T) bases of the third strand consisting of the oligonucleotide and, secondly, AT base pairs of the double-stranded DNA, so as to form T*AT triads. Similarly, protonated cytosines located in the third strand pair with GC base pairs of the double-stranded DNA so as to form ⁺C*GC triads (Sun et al., *Curr. Opin Struc Biol.* 3 (1993) 345). It has so far been established that these T*AT and ⁺C*GC triads (named canonical triads) ensure maximum stability of the triple helix. However, many other factors are also involved in the stabilization of the triple helix, such as for example the percentage of cytosines, the pH, the salinity of the medium or the environment of the triple helix. It is also widely described that the introduction of triads termed noncanonical (i.e. different from the T*AT and ⁺C*GC triads) causes a more or less considerable structural deformation in the triple helix and systematically leads to significant destabilization thereof. The introduction of various noncanonical triads has, moreover, been studied in the context of comparative studies (Roberts et al., *Proc. Natl. Acad. Sci. USA* 88, 9397; Fossella et al., (1993) *Nucleic Acids Research* 21, 4511; Govers et al., *Nucleic Acids Research* (1997) 25, 3787) showing variable destabilization of the triple helix as a function of the nature of the noncanonical triad introduced.

While this process allows rapid and efficient purification of a target DNA of pharmaceutical quality, it requires however a sufficiently long, preferably totally homopurine, sequence to be present on one of the two strands of the DNA to be purified, and to be complementary to the third DNA strand. This sequence may be naturally present in, or be inserted artificially into, the target double-stranded DNA sequence, the purification of which is desired.

The applicant has now discovered, surprisingly and unexpectedly, that a DNA molecule bearing, on one strand, a target DNA sequence not essentially composed of purine bases is also capable of forming a stable triple helix structure with a third DNA strand, despite the presence of bases which are not complementary to those of the oligonucleotide producing the formation of noncanonical triads.

More precisely, the target double-stranded DNA sequences newly identified by the applicant comprise, on one strand, a homopurine sequence interrupted with a given number of pyrimidine bases. The applicant has also discovered that these partly homopurine-partly homopyrimidine DNA sequences can be used to efficiently purify the DNA molecules containing them, by triple helix interaction.

The newly identified sequences are also particularly useful for detecting, quantifying, isolating or sorting DNA molecules containing them.

A subject of the present invention is therefore novel target DNA sequences comprising, on one strand, a sequence having the following general formula:

$$5'\text{-}(R)_n\text{---}(N)_t\text{---}(R')_m\text{-}3'$$

in which:
R and R' represent nucleotides composed only of purine bases;
n and m are integers less than 9, and the sum of n+m is greater than 5;
N is a nucleotide sequence comprising both purine bases and pyrimidine bases;
t is an integer less than 8;

said DNA sequence being capable of interacting with a third DNA strand and thus of producing the formation of a triple helix structure.

The homopurine sequences R and R' located in the 5' and 3' portions, respectively, of the target DNA sequence therefore have a total length greater than or equal to 6. They comprise adenine and guanine bases capable of interacting with a third strand in order to produce the formation of a triple helix structure consisting of T*AT and $^+$C*GC canonical triads. Preferably, the homopurine sequences R and R' comprise at least 2 guanines in total and at least 2 adenines. Even more preferably, these purine sequences comprise a motif of the (AAG) type.

The central sequence N is less than 8 pairs of purine and pyrimidine bases in length t, and is capable, according to the invention, of interacting with a third DNA strand in order to produce the formation of noncanonical triads. Preferably, the length of the central sequence N is greater than or equal to 1, and less than 8. Even more preferably, the length of the central sequence N is greater than or equal to 2, and less than 8.

The term "canonical triad" is intended to mean the two nucleotide triads resulting from the interaction of the AT and GC doublets of the double-stranded DNA, with the T and $^+$C bases so as to give the T*AT and $^+$C*GC triads, respectively. These two triads are, among the 16 existing triads, those which have the greatest stability.

The term "noncanonical triad" is intended to mean the set of 14 other nucleotide triads. They result from the interaction of a double-stranded DNA with a third DNA strand, in a nonspecific way, and exhibit decreased stability with respect to the T*AT and $^+$C*GC canonical triads. Mention may be made in particular of the T*CG and T*GC noncanonical triads which are formed, respectively, by interaction between a CG or GC doublet of the target sequence and thymine (T) of the third strand, the G*CG noncanonical triad resulting from the interaction between a CG doublet of the target sequence and a guanine (G) of the third strand, the C*AT and C*TA noncanonical triads which result from the interaction, respectively, of the AT and TA doublets of the target sequence and of cytosines (C) located on the third strand, the G*CG noncanonical triad which is formed by interaction of a CG doublet with a guanine (G) of the third strand, or the T*TA triad which results from the interaction of a TA doublet with a thymine (T) of the third strand.

It is clearly understood that, like the purine ends in 5' and in 3', the central sequence N can also form T*AT and $^+$C*GC canonical triads resulting from the respective interaction of AT and GC doublets with thymine (T) and cytosine (C) bases located on the third DNA strand.

Preferably, the central sequence N comprises purine and pyrimidine bases which produce the formation of at most 6 noncanonical triads. More preferably, the noncanonical triads resulting from the interaction of the central portion with the oligonucleotide are chosen from the T*CG, T*GC, C*AT and C*TA noncanonical triads. By way of examples of preferred distributions of these triads, mention may be made of the formation of six noncanonical triads comprising a C*AT, a C*TA, two T*CGs and two T*GCs, the formation of five noncanonical triads comprising two C ATs and three T*GCs, or the formation of three noncanonical triads comprising two T*GCs and one C*AT. Several T*TA noncanonical triads may also be present but, in this case, they are not positioned consecutively in the triple helix.

The central sequence preferably comprises at most three C or T pyrimidine bases producing the formation of the T*CG and C*TA or G*TA noncanonical triads. Preferably, the three pyrimidine bases are not consecutive but are separated by A or G purine bases, which can interact with the third DNA strand so as to form the T*GC and C*AT noncanonical bases and also the TAT and $^+$C*GC canonical triads.

According to a particular embodiment of the invention, the target double-stranded DNA sequence is the sequence 5'-AA GAA GCA TGC AGA GAA GAA-3' (SEQ ID NO: 1).

The third DNA strand which is capable of interacting with the double-stranded DNA sequences according to the invention perhaps, for example, an oligonucleotide or the strand of another double-stranded DNA, in the locally unpaired state, and can contain the following bases:

thymine (T), which is capable of forming T*AT canonical triads with the AT doublets of the target double-stranded DNA sequence, and also T*CG and T*GC noncanonical triads with the CG and GC doublets, respectively, of the target DNA sequence (Soyfer et al., in *Triple Helical Nucleic Acids* (1996) Springer, N.Y., pp. 151-193);

guanine (G), which is capable of forming G*TA triads with the TA doublets of the double-stranded DNA (Soyfer et al., in Triple Helical Nucleic Acids (1996) Springer, N.Y., pp.151-193);

cytosine (C), which is capable of forming $^+$C*GC (protonated cytosine C$^+$) canonical or C*AT and C*TA noncanonical triads with the GC, AT and TA doublets, respectively, of the target double-stranded DNA; and uracil, which is capable of forming triplets with the AU or AT base pairs of the target sequence (Bates et al., *Nucleic Acids Research* 23 (1995) 3627).

Preferably, the third DNA strand used comprises a homopyrimidine sequence rich in cytosines, which are present in the protonated state at acid pH and stabilize the triple helix. Such oligonucleotides can, for example, comprise the (CCT)n sequence, the (CT)n sequence or the (CTT)n sequence, in which n is an integer between 1 and 20 inclusive. It is particularly advantageous to use sequences of the (CT)n or (CTT)n type, or sequences in which (CCT), (CT) or (CTT) motifs are combined.

When the third DNA strand is present in the form of an oligonucleotide, the latter may be natural, i.e. composed of natural, unmodified bases, or be chemically modified. In particular, the oligonucleotide can advantageously have certain chemical modifications making it possible to increase its resistance to or its protection against nucleases, or its affinity with respect to the specific sequence.

According to the present invention, the term "oligonucleotide" is intended to mean any chain of nucleosides having undergone a modification of the backbone with the aim of making it more resistant to nucleases. Among the possible modifications, mention may be made of phosphorothioate oligonucleotides which are capable of forming triple helices with DNA (Xodo et al., *Nucleic Acids Research*, 22 (1994) 3322), as well as oligonucleotides having formacetal or methyl phosphonate backbones (Matteucci et al., *J. Am. Chem. Soc.*, 113 (1991) 7767). It is also possible to use oligonucleotides synthesized with α-anomers of nucleotides, which also form triple helices with DNA (Le Doan et al., *Nucleic Acids Research*, 15 (1987) 7749). Another modification of the backbone is the phosphoramidate linkage. Mention may be made, for example, of the phosphoramidate N3'-P5' internucleotide linkage described by Gryaznov et al. (*J. Am. Chem. Soc.*, 116 (1994) 3143), which gives oligonucleotides which form particularly stable triple helices with DNA. Among the other modifications to the backbone, mention may also be made of the use of ribonucleotides, of 2'-O-methylribose, or of a phosphodiester (Sun et al., *Curr. Opinion in Struct. Biol.*, 3 (1993) 3143). Finally, the phosphorous backbone can be replaced with a polyamide backbone as in PNAs (Peptide Nucleic Acids), which can also form triple helices (Nielsen et al., *Science*, 254 (1991), 1497; Kim et al., *J. Am. Chem. Soc.*, 115 (1993) 6477-6481).

The thymine of the third strand can also be replaced with a 5-bromouracil, which increases the affinity of the oligonucleotide for DNA (Povsic et al., *J. Am. Chem. Soc.*, 111 (1989) 3059). The third strand can also contain unnatural bases, among which mention may be made of 7-deaza-2'-deoxyxanthosine (Milligan et al., *Nucleic Acids Res.*, 21 (1993) 327), 1-(2-deoxy-alpha-D-ribofuranosyl)-3-methyl-5-amino-1H-pyrazolo[4,3-d]pyrimidine-7-one (Koh et al., *J. Am. Chem. Soc.*, 114 (1992) 1470), 8-oxoadenine, 2-aminopurine, 2'-O-methylpseudoisocytidine or any other modification known to those skilled in the art (Sun et a., *Curr. Opinion in Struct. Biol.*, 3 (1993) 345).

The object of another type of modification of the third strand is more particularly to improve the interaction and/or the affinity between the third strand and the specific sequence. In particular, an entirely advantageous modification according to the invention consists in methylating the cytosines of the oligonucleotide in the 5 position. The oligonucleotide thus methylated has the notable property of forming a stable triple helix with the specific sequence, in pH ranges closer to neutrality ($\geq 5$; Xoda et al., *Nucleic Acids Research* 19 (1991) 5625). It therefore makes it possible to work at higher pHs than the oligonucleotides of the prior art, i.e. at pHs at which the risks of degradation of the plasmid DNA are considerably less.

The length may be adjusted case by case by those skilled in the art, as a function of the desired selectivity and stability of the interaction.

The third DNA strands according to the invention can be synthesized by any known technique. In particular, they can be prepared by means of nucleic acid synthesizers. Any other method known to those skilled in the art can of course be used.

These third DNA strands or these oligonucleotides are capable of forming a triple helix with a specific double-stranded DNA sequence as described above, comprising a mixed (pyrimidine-purine) internal region N less than 8 nucleotides long, flanked by two homopurine regions R and R'. The latter may, for example, comprise a motif of the GAA type.

By way of example, mention may be made of the target double-stranded DNA sequence corresponding to the sequence: 5'-AA GAA GCA TGC AGA GAA GAA-3' (SEQ ID NO: 1), which is capable of forming a triple helix with an oligonucleotide comprising a sequence chosen from the following sequences: 5'-TT CTT CTT CTT CTT CTT CTT-3' (SEQ ID NO: 2), 5'-TT CTT CTT GCT TCT CTT CTT-3' (SEQ ID NO: 3), 5'-TT CTT CTT GTT TCT CTT CTT-3' (SEQ ID NO: 4), and 5'-TT CTT CTT CCT TCT CTT CTT-3' (SEQ ID NO: 5).

The formation of the triple helix may be obtained in the presence of $Mg^{2+}$ ions which may optionally promote the stabilization of this structure (Vasquez et al., Biochemistry 34 (1995) 7243; Beal et al., *Science* 251 (1991) 1360).

According to a preferred embodiment, the target DNA sequences according to the invention can be naturally present on the double-stranded DNA, and it is then particularly advantageous to use an oligonucleotide capable of forming a triple helix with such a sequence present, for example, in the sequence of genes of interest, such as genes of therapeutic or experimental interest, or marker genes. In this respect, the applicant has analyzed the nucleotide sequences of various genes of interest and has tested the stability of the triple helix interactions with an oligonucleotide of the (CTT)n type, and it has been able to show that certain regions of these genes produce the formation of a stable triple helix despite the presence of noncanonical triads such as T*CG, T*GC, C*AT, C*TA and T*TA.

Among the sequences which are naturally present on a double-stranded DNA, mention may be made of the 5'-AA GAA GCA TGC AGA GAA GAA-3' sequence (designated ID1) (SEQ ID NO: 1) present in the sequence of the human FGF1 gene (Jaye et al., *Science* 233 (1986) 541), the 5'-GAA GAA GCA CGA GAA G-3' sequence (SEQ ID NO: 6) of the human gene encoding factor IX involved in clotting (Kurachi et al., *Proc. Natl. Acad. Sci. U.S.A.* 79 (1982) 6461), the 5'-AAA GAA AGC AGG GAA G-3' (SEQ ID NO: 7) and 5'-GAA GAG GAA GAA G-3' (SEQ ID NO: 8) sequences of the SeAP secreted alkaline phosphatase gene (Millan et al., *J. Biol. Chem.*, 261 (1986) 3112), the 5'-AAG GAG AAG AAG AA-3' sequence (SEQ ID NO: 9) of the human alpha fetoprotein hαFP gene (Gibbs et al., *Biochemistry* 26 (1987) 1332), the 5'-AA GAT GAG GAA GAA G-3' sequence (SEQ ID NO: 10) of the human GAX gene for controlling restenosis (Gorski et al., *Mol. Cell. Biol.*, 13 (1993) 3722) and, finally, the 5'-GGC AAC GGA GGA A-3' sequence (SEQ ID NO: 13) of the human VEGFB-167 gene (Olofsson et al., *J. Biol. Chem.*, 271 (1986) 19310). The formation of a triple helix with a sequence present in a gene of therapeutic or experimental interest is particularly advantageous since it is not necessary to modify the target double-stranded DNA or the plasmid carrying this gene so as to incorporate into it an artificial specific sequence.

A second aspect of the present invention is based on a process for purifying double-stranded DNA, according to which a solution containing a DNA, mixed with other components, is brought into contact with a third DNA strand as described above, which is then preferably an oligonucleotide capable of forming, by hybridization, a triple helix with a specific sequence present on the double-stranded DNA as described above. Preferably, the double-stranded DNA is brought into contact in solution with the oligonucleotide immobilized on a support. Even more preferably, the oligonucleotide is covalently coupled to said support. Thus, the step for bringing a solution containing a double-stranded DNA into contact can advantageously consist in passing the solution of DNA, mixed with other components, over the support to which the oligonucleotide is coupled, in order to obtain the double-stranded DNA, the purification of which is desired, in an efficient and rapid manner.

Such supports are well known to those skilled in the art and comprise, for example, consisting of beads or of microparticles, such as latex particles, or of any other support in suspension. The oligonucleotide can also be grafted onto a molecule of the polymer type of natural or synthetic origin. Preferably, the polymer to which the oligonucleotide is attached has a property which allows it to be easily separated from the solution after formation of the triple helix with the double-stranded DNA. Among natural polymers, mention may be made of proteins, lipids, sugars and polyols. Among synthetic polymers, mention may be made of polyacrylamides, polyethylene glycols, styrene derivatives and heat-sensitive polymers such as, for example, compounds of the type poly(N-isopropylacrylamide), which are soluble at low temperature and become insoluble above their phase transition temperature (T. Mori et al., *Biotechnology and Bioengineering*, 72 (2001) 261).

The purification process according to the present invention is particularly useful since it enables the purification i) of DNA molecules which do not contain a homopurine sequence of sufficiently great length to allow the formation of a stable triple helix structure with a homopyrimidine oligonucleotide, but also ii) the DNA molecules in which the homopurine sequence is interrupted with several pyrimidine bases. In addition to allowing the purification of a greater variety of DNA molecules, this process is also rapid and produces yields and degrees of purity which are particularly high.

Moreover, it makes it possible to purify DNA molecules from complex mixtures comprising other nucleic acids, proteins, endotoxins (such as lipopolysaccharides), nucleases, etc., and to obtain a purified DNA of pharmaceutical quality.

In order to allow its covalent coupling to the support, the oligonucleotide is generally functionalized. Thus, it may be modified with a terminal thiol, amine or carboxyl group, in the 5' or 3' position. In particular, the addition of a thiol, amine or carboxyl group makes it possible, for example, to couple the oligonucleotide to a support bearing disulfide, maleimide, amine, carboxyl, ester, epoxide, cyanogen bromide or aldehyde functions. These couplings are formed through the establishment of disulfide, thioether, ester, amide or amine attachments between the oligonucleotide and the support. Any other method known to those skilled in the art can be used, such as difunctional coupling reagents for example.

Moreover, in order to improve the hybridization with the coupled oligonucleotide, it may be advantageous for the oligonucleotide to contain an "arm" and a "spacer" sequence of bases. The use of an arm in fact makes it possible to attach the oligonucleotide at a chosen distance from the support, making it possible to improve the conditions of interaction with the DNA. The arm advantageously consists of a linear carbon-based chain comprising 1 to 18, and preferably 6 to 12, groups of $CH_2$ type, and an amine which allows the attachment to the column. The arm is linked to a phosphate of the oligonucleotide or of a "spacer" composed of bases which are not involved in the hybridization. Thus, the "spacer" can comprise purine bases. By way of example, the "spacer" can comprise the sequence GAGG (SEQ ID NO: 21).

The oligonucleotide coupled to the purification support can, for example, have the sequence 5'-GAGG CTT CTT CTT CTT CTT CTT CTT-3' (GAGG (CTT)$_7$; SEQ ID NO: 11) in which the GAGG bases are not involved in a triple helix structure, but make it possible to form a space between the oligonucleotide and the coupling arm.

Various types of support can be used for carrying out the present invention. They may be functionalized chromatography supports, loose or prepackaged in columns, functionalized plastic surfaces or functionalized latex beads, which may or may not be magnetic. They are preferably chromatography supports. By way of example, chromatography supports which can be used are agarose, acrylamide or dextrans, and also derivatives thereof (such as Sephadex®, Sepharose®, Superose®, etc.), polymers such as poly(styrenedivinylbenzene), or grafted on nongrafted silica, for example. The chromatography columns can function in diffusion or perfusion mode, or in a "fluidized bed" or "expanded" system, using a chromatography support with a density which is suitable for this particular embodiment.

The process according to the present invention can be used to purify any type of double-stranded DNA. This is, for example, circular DNA, such as a minicircle (Darquet et al., Gene Therapy 6 (1999) 209), a linear fragment, or a plasmid carrying generally one or more genes of therapeutic or experimental interest. This plasmid may also carry an origin of replication, for example of the conditional type (such as the pCOR plasmids which are described by Soubrier et al., Gene Therapy 6 (1999) 1482), a marker gene, etc. The process of the invention can be applied directly to a cell lysate. In this embodiment, the plasmid, amplified by transformation and then cell culture, is purified directly after cell lysis. The process according to the invention can also be applied to a clear lysate, i.e. to the supernatant it obtained after neutralization and centrifugation of the cell lysate. It can, of course, also be applied to a solution which is prepurified using known methods. This process also makes it possible to purify linear or circular DNA carrying a sequence of interest, from a mixture comprising DNAs of various sequences. The process according to the invention can also be used for purifying double-stranded RNA.

The cell lysate can be a lysate of prokaryotic or eukaryotic cells. Regarding prokaryotic cells, mention may be made, for example, of *E. coli, B. subtilis, S. typhimurium, S. aureus* or *Streptomyces bacteria*. Regarding eukaryotic cells, mention may be made of animal cells, yeasts, fungi, etc., and more particularly *Kluyveromyces* or *Saccharomyces* yeasts, or COS, CHO, CI27, NIH3T3, MRC5, 293, etc. cells.

The process of the invention is particularly advantageous since it makes it possible to obtain, rapidly and simply, plasmid DNA of very high purity. In particular, as illustrated in the examples, this process makes it possible to efficiently separate plasmid DNA from contaminating components such as fragmented chromosomal DNA, RNAs, endotoxins, proteins or nucleases.

The process of the invention is also useful for purifying and enriching DNA molecules, and particularly genes of therapeutic interest, such as the FGF1 gene, which are produced and purified on an industrial scale, and the purity of which must be compatible with pharmaceutical use.

According to a third aspect, a subject of the present invention is a process for detecting, quantifying and sorting double-stranded DNA molecules comprising at least one target sequence as described above, which consists a) in bringing a solution suspected of containing said molecules into contact with a third DNA strand, for example a labeled oligonucleotide, so as to form a stable triple helix, and b) in detecting the complex possibly formed between the double-stranded DNA and the third DNA strand.

This process is useful in particular in the context of the analysis of genomes, by allowing, for example, the detection of a particular DNA sequence in a genome or the sorting of specific sequences.

The third DNA strand or the oligonucleotide, according to this aspect of the present invention, can be labeled by incorporating a label which is detectable by spectroscopic, photochemical, biochemical, immunochemical or chemical means. For example, such labels can consist of radioactive isotopes ($^{32}$P, $^{33}$P, $^{3}$H, $^{35}$S) or fluorescent molecules (5-bromodeoxyuridine, fluorescein, acetylaminofluorene, digoxigenin).

The labeling is preferably carried out by incorporating labeled molecules into the polynucleotides by primer extension, or by adding to the 5' or 3' ends.

Examples of nonradioactive labeling are described in particular in French patent No. FR 78 109 75, or in the articles by Urdea et al. (1988, *Nucleic Acids Research*, 11: 4937-4957) or Sanchez-pescador et al. (1988; *J. Clin. Microbiol.*, 26(10): 1934-1938).

According to this particular aspect of the present invention, the third DNA strand or the oligonucleotide can also be immobilized on a support as described above.

A fourth aspect of the present invention relates to a pack or kit for purifying and/or detecting the presence of a double-stranded DNA according to the invention in a complex mixture, said pack comprising one or more oligonucleotides as described above. The latter can be immobilized on a support and/or comprise a detectable label.

According to this aspect of the present invention, the detection kit described above, such as kit will comprise a plurality of oligonucleotides in accordance with the invention which may be used to detect target double-stranded DNA sequences of interest.

Thus, the oligonucleotides immobilized on a support can be organized in matrices such as "DNA chips". Such organized matrices have in particular been described in U.S. Pat. No. 5,143,854, and in PCT applications No. WO 90/15070 and 92/10092.

Support matrices on which the oligonucleotides have been immobilized at a high density are, for example, described in U.S. Pat. No. 5,412,087 and in PCT application No. WO 95/11995.

The present application will be described in greater detail using the examples which follow, which should be considered as illustrative and nonlimiting.

LEGEND OF THE FIGURES

Figure 2:
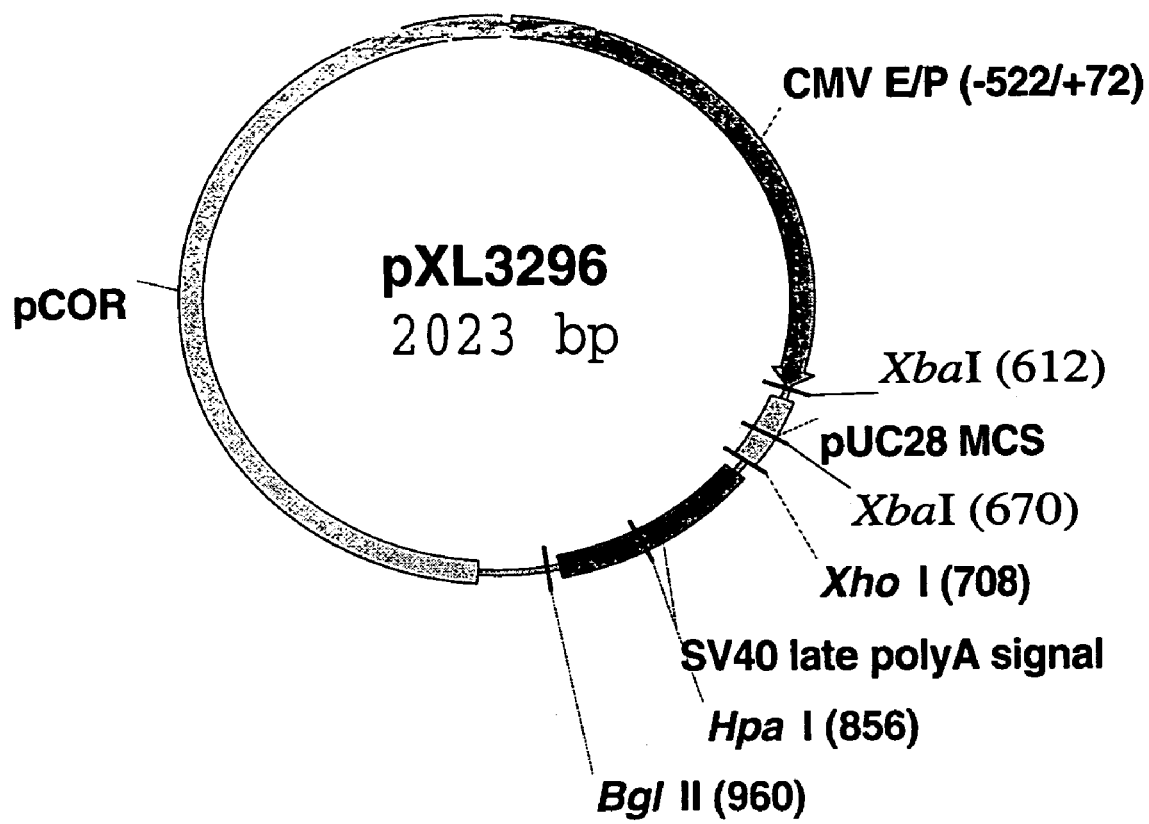
Figure 3:
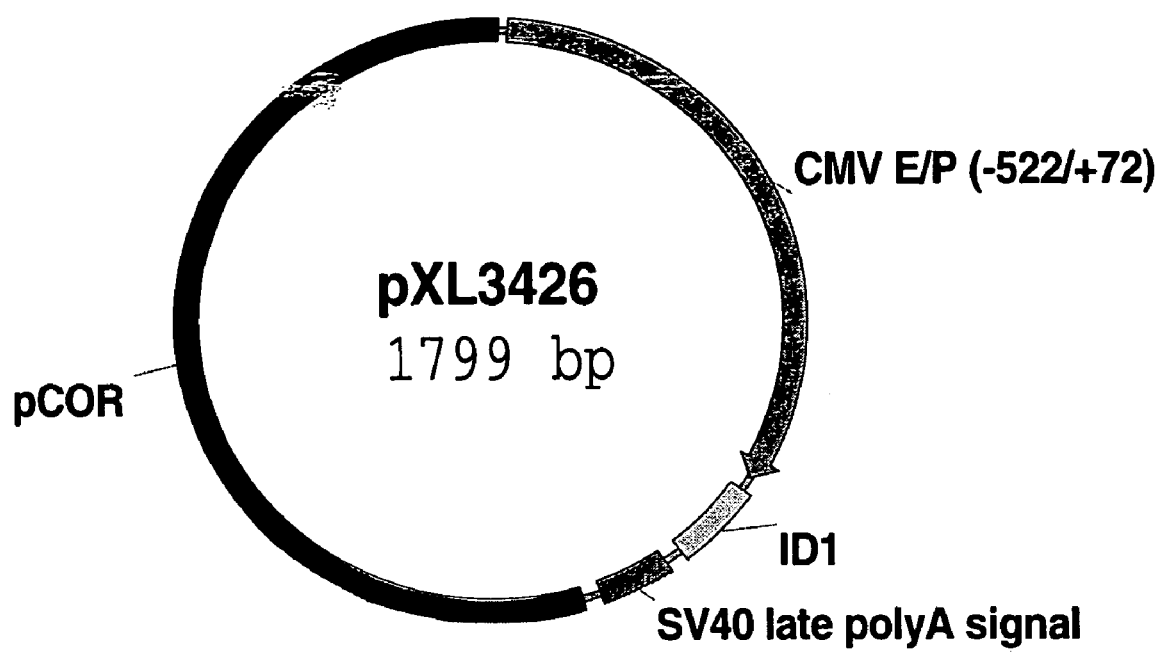
Figure 4:
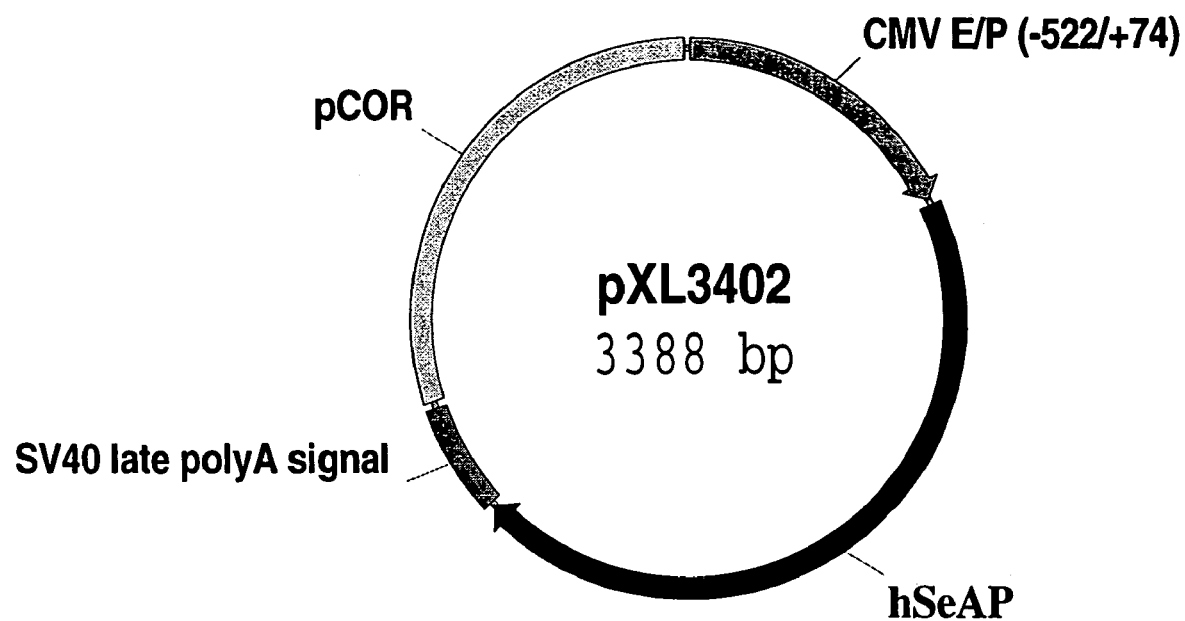
Figure 5:
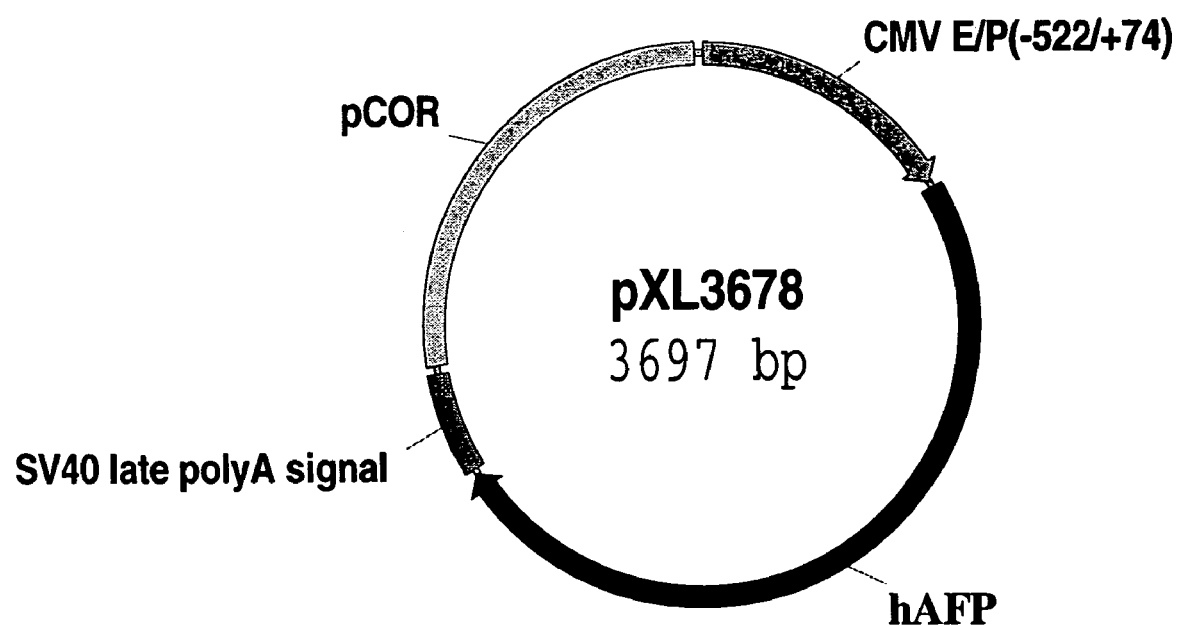
Figure 6:
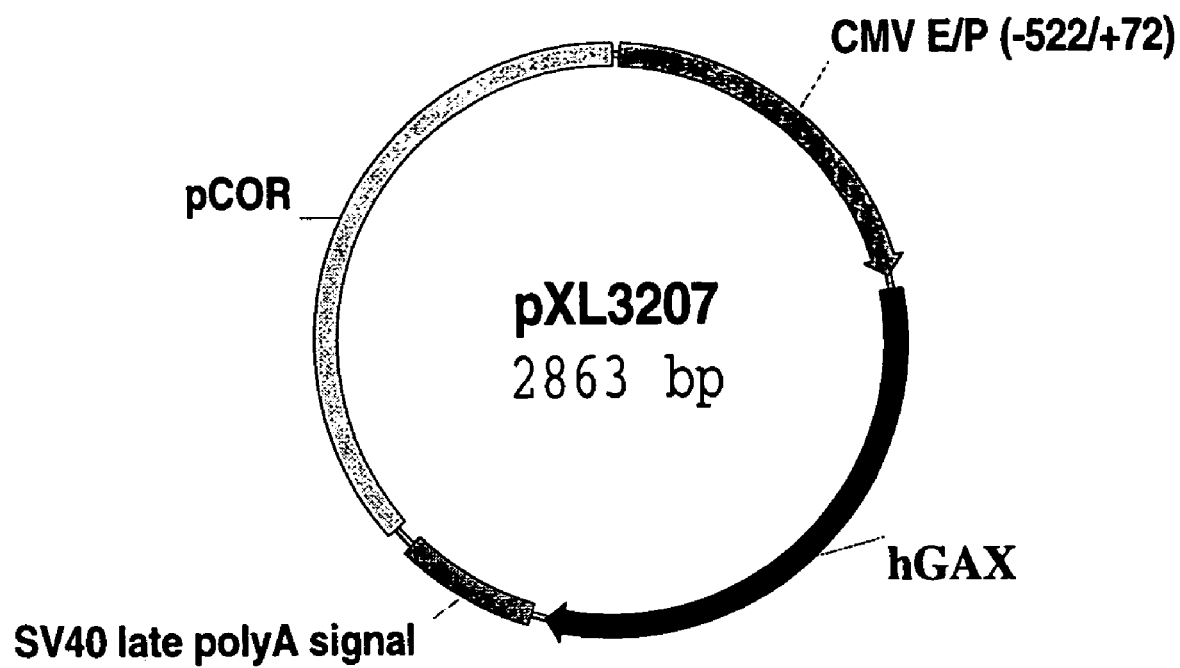
Figure 7:
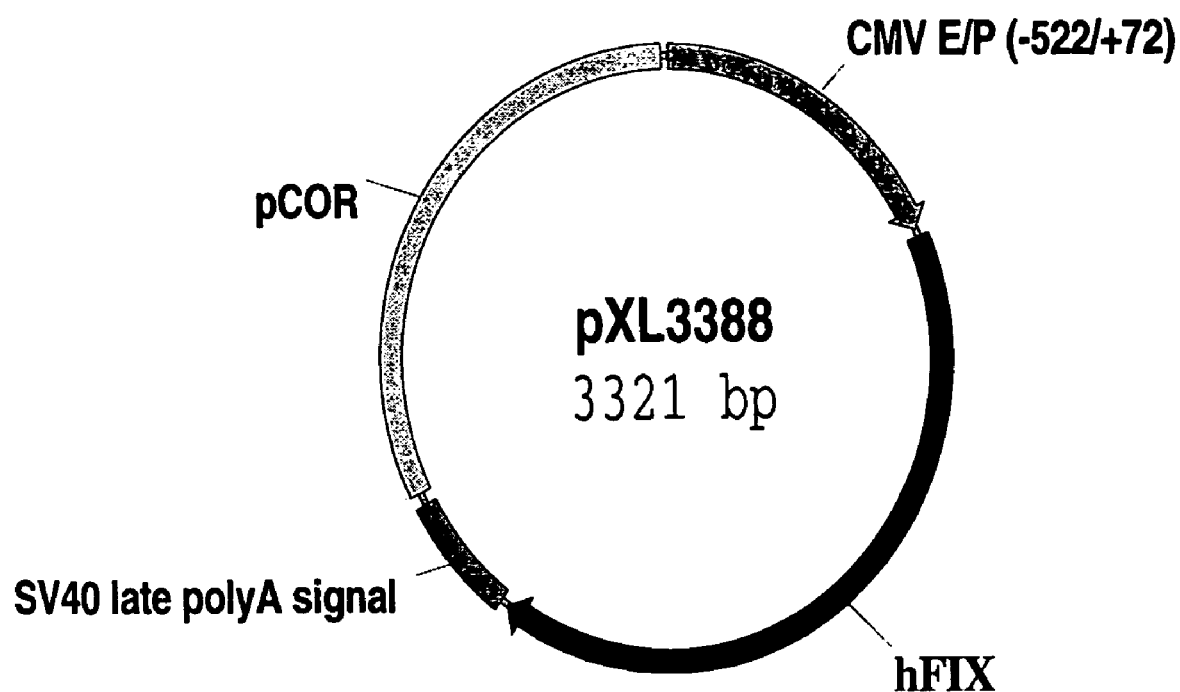
Figure 8:
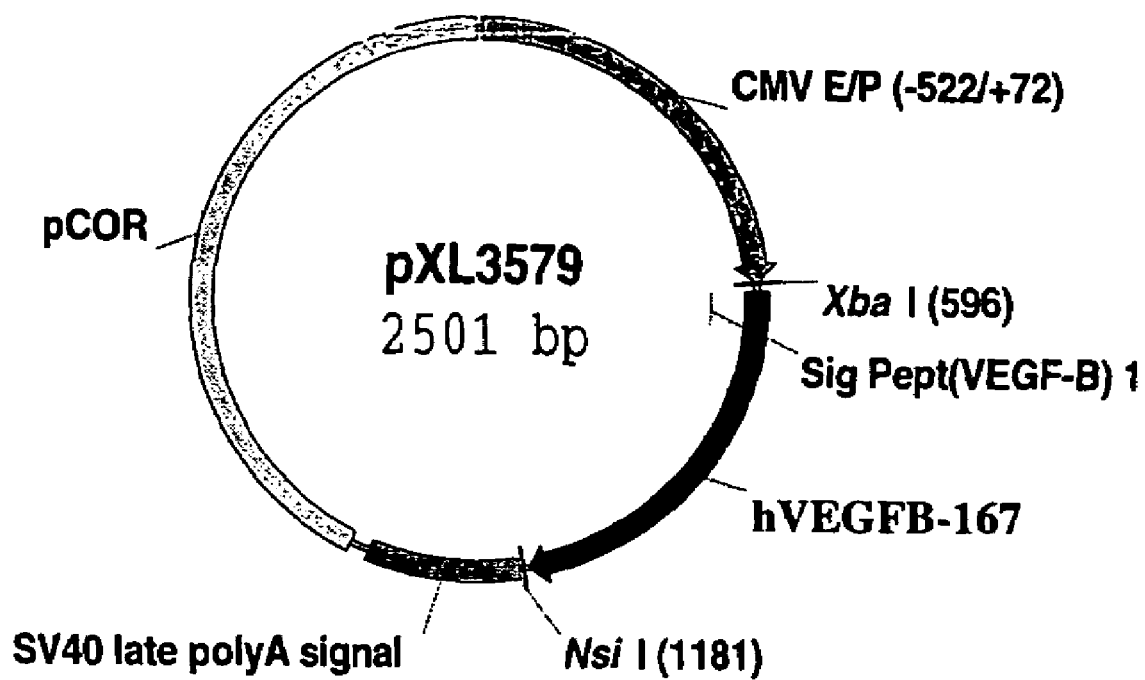
Figure 9:
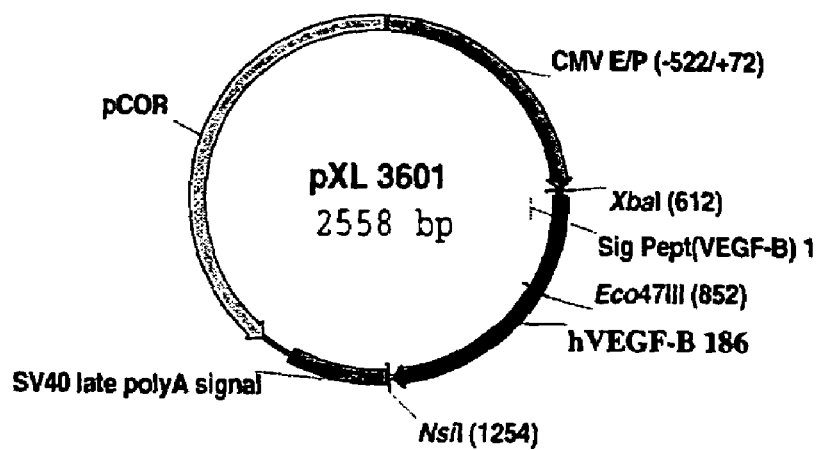
Figure 9:
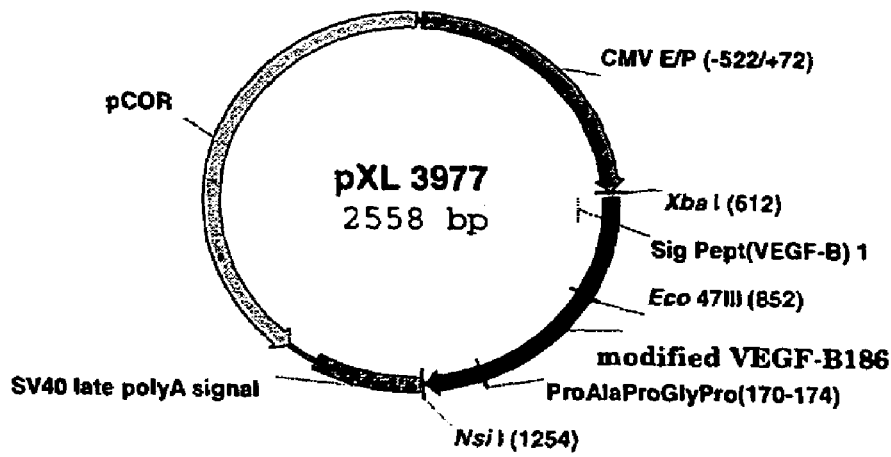

FIG. 1: Schematic representation of the plasmid pXL3179;
FIG. 2: Schematic representation of the plasmid pXL3296;
FIG. 3: Schematic representation of the plasmid pXL3426;
FIG. 4: Schematic representation of the plasmid pXL3402;
FIG. 5: Schematic representation of the plasmid pXL3678;
FIG. 6: Schematic representation of the plasmid pXL3207;
FIG. 7: Schematic representation of the plasmid pXL3388;
FIG. 8: Schematic representation of the plasmid pXL3579.
FIG. 9: Schematic representations of the plasmids pXL3601 and pXL3977.

GENERAL CLONING AND MOLECULAR BIOLOGY TECHNIQUES

The conventional methods of molecular biology, such as digestions with restriction enzymes, gel electrophoresis, DNA fragment ligation, transformation in *E. coli*, precipitation of nucleic acids, sequencing, etc., are described in the literature (Maniatis et al., (1989) Molecular cloning: a laboratory manual, second edition, Cold Spring Harbor Laboratory, Cold Spring Harbor Laboratory Press, New York; Ausubel et al., (1987) Current protocols in molecular biology, John Willey and Sons, New York). The restriction enzymes were supplied by New-England Biolabs, Beverly, Mass. (Biolabs).

The oligonucleotides are synthesized using the chemistry of phosphoramidites protected in the α position with a cyanoethyl group (Sinha et al. *Nucleic Acids Research*, 12 (1984) 4539; Giles (1985), with the 394 automatic DNA synthesizer from the company Applied Biosystem using the manufacturer's recommendations.

The oligonucleotides used for synthesizing affinity gels are obtained from the company Amersham Pharmacia Biotech (Uppsala, Sweden) or from Eurogentec (Seraing, Belgium), and are used without modification.

The strains allowing the replication of the pCOR plasmids, and the conditions for growth and for selection of these plasmids, have already been described (Soubrier et al., *Gene Therapy* 6 (1999) 1482).

EXAMPLE 1

Construction of Plasmids

1.1 The Plasmid pXL3179 (pCOR-FGF1)

The plasmid pXL3179, which is represented in FIG. 1, is a vector derived from the plasmid pXL2774 (WO 97/10343; Soubrier et al., *Gene Therapy* 6 (1999) 1482) into which the gene encoding a fusion between the signal peptide of human fibroblast interferon and the FGF1 (Fibroblast Growth Factor 1) cDNA (sp-FGF1, Jouanneau et al., *PNAS* 88 (1991) 2893) has been introduced under the control of the promoter originating from the early region of the human Cytomegalovirus (hCMV IE E/P) and of the polyadenylation signal of the SV40 virus late region (SV40 late polyA; Genbank SC4CG).

1.2 The Plasmid pXL 3296 (pCOR)

The plasmid pXL3296 derives from the plasmid pXL3179 in which the sequence of the sp-FGF1 gene has been replaced with the multiple cloning site of the plasmid pUC28 (Benes et al., *Gene* 130 (1993) 151). The plasmid pXL2396 is represented in FIG. 2.

1.3 The Plasmid pXL3426 (pCOR-ID1)

The plasmid pXL3426 derives from the plasmid pXL3296 into which the sequence 5'-GATCCAAGAAGCATGCA-GAGAAGAATTC-3' (SEQ ID NO: 17) has been inserted between the Bg/II and XhoI sites. The plasmid pXL 3426 is represented in FIG. 3.

EXAMPLE 2

Construction of Other Plasmids Carrying Target Sequences

The plasmid pXL3675 derives from the plasmid pXL3296 into which the sequence 5'-GAAGAAGGGAAAGAA-GATCTG-3' (SEQ ID NO: 18) has been inserted between the HpaI and XbaI sites; the plasmid pXL3676 also derives from the plasmid pXL3296, in which the sequence 5'-GAA-GAAAGGAGAGAAGATCTG-3' (SEQ ID NO: 19) has been inserted between HpaI and XbaI, and finally the plasmid pXL3713 which contains the DNA sequence 5'-GAA-GAAGTTTAAGAAGATCTG-3' (SEQ ID NO: 20) inserted between the HpaI and XbaI sites of pXL3296. The plasmids thus constructed were purified by CsCI chloride gradient, and the sequence of the inserts was confirmed by sequencing. These preparations were used in the examples described hereinafter.

EXAMPLE 3

Identification of a 20-mer Sequence Internal to the FGF1 Gene, Forming a Stable Triple Helix The various plasmids as described in the examples which follow were chromatographed by triple helix interaction affinity chromatography under standardized conditions. The affinity support was synthesized in the following way, using the chromatography support Sephacryl® S-1000 SF (Amersham Pharmacia Biotech). In a first step, the Sephacryl® S-1000 gel dispersed in a 0.2 M sodium acetate buffer was activated with sodium meta-periodate (3 mM, 20° C., 1 h) and then, in a second step, the oligonucleotide was coupled, through its 5'-NH$_2$-terminal portion, to the aldehyde groups of the activated matrix via a reductive amination reaction in the presence of ascorbic acid (5 mM), following a procedure similar to that described for the coupling of proteins (Hornsey et al., *J. Immunol. Methods* 93 (1986) 83). For all the experiments reported in the present invention, the oligonucleotides were coupled by following this general procedure; all the oligonucleotides have an NH$_2$—(CH$_2$)$_6$— functionalized arm located at the 5' end of the oligonucleotide.

The experiments directed toward demonstrating the formation of a triple helix structure between an oligonucleotide and a double-stranded DNA, and toward measuring the stability, were all carried out under the following conditions. In each experiment, 300 µg of purified plasmid dissolved in 6 ml of 50 mM sodium acetate buffer (pH 4.5) containing 2 M NaCl was injected, at a flow rate of 30 cm/h, onto an HR 5/5 column (Amersham Pharmacia Biotech) containing 1 ml of affinity gel functionalized with an oligonucleotide according to the invention. After washing the column with 5 ml of the same buffer, the plasmid was eluted with 3 ml of 100 mM Tris/HCl column buffer (pH 9.0) containing 0.5 mM EDTA, and the amount of plasmid eluted by the pH 9.0 buffer was quantified, i) by measuring the absorbence at 260 nm of the solution and ii) by anion exchange chromatography on a Millipore Gen-Pak-Fax column (Marquet et al., BioPharm, 8 (1995) 26).

Using a column functionalized with the oligonucleotide 5'-NH$_2$-(CH$_2$)$_6$-TT(CTT)$_6$-3' (SEQ ID NO: 2), the results of the purification which are given in Table 1 below demonstrate the formation of a stable triple helix with the plasmids comprising either the entire FGF1 gene (pXL3179), or an internal ID1 sequence of the human FGF1 gene (pXL3426), in contrast with a control plasmid (pXL3296) which comprises no sequence of the human FGF1 gene and which is not retained on the column in question.

TABLE 1

| Plasmids | Sequence of the oligonucleotide Target sequence in the plasmid | Capacity (µg plasmid attached per ml of gel) |
|---|---|---|
| pXL3179(pCOR-FGF1) | TT CTT CTT CTT CTT CTT CTT (SEQ ID NO: 2) | 175 |
| pXL3426(pCOR-ID1) | TT CTT CTT CTT CTT CTT CTT (SEQ ID NO: 2) AA GAA GCA TGC AGA GAA GAA (SEQ ID NO: 1) | 130 |
| pXL3296(pCOR) | TT CTT CTT CTT CTT CTT CTT (SEQ ID NO: 2) | <1 |

Using a column functionalized with the oligonucleotide 5'-NH$_2$-(CH2)$_6$-TT(CTT)$_6$-3' (SEQ ID NO: 2), the results of the purification which are given in Table 1 below demonstrate the formation of a stable triple helix with the plasmids comprising either the entire FGF1 gene (pXL3179), or an internal ID1 sequence of the human FGF1 gene (pXL3426), in contrast with a control plasmid (pXL3296) which comprises no sequence of the human FGF1 gene and which is not retained on the column in question.

EXAMPLE 4

Identification of the Bases Required, in the Internal ID1 20-mer Sequence Internal to the FGF1 Gene, for the Stability of the Triple Helix Structure Four 4-oligonucleotides were prepared based on the internal ID1 sequence. For two of them, 7 or 13 nucleotides are absent from the 5' side of ID1, and for the other 2, 7 or 14 nucleotides are absent from the 3' side. The plasmid pXL3426 was chromatographed on a triple helix interaction column functionalized using the oligonucleotide 5'-TT(CTT)$_6$-3' (SEQ ID NO: 2) or the oligonucleotides FRB36, FRB38, FRB39 or FRB40. The stability of the triple helix structure formed with the various truncated internal ID1 sequences was then tested by measuring the amount of each of the plasmids retained on the column.

TABLE 2

| Oligonucleotide | Sequence targeted in the plasmid pXL3426 | Capacity (µg plasmid attached per ml of gel) |
|---|---|---|
| (CTT)7 | AA GAA GCA TGC AGA GAA GAA (SEQ ID NO: 1) | 130 |
| FRB36 | -----A GAA GAA (SEQ ID NO: 22) | <1 |
| FRB38 | AA GAA G----- (SEQ ID NO: 23) | <1 |
| FRB39 | AA GAA GCA TGC AG--- (SEQ ID NO: 24) | 22 |
| FRB40 | ---A TGC AGA GAA GAA (SEQ ID NO: 25) | 33 |

The results given in Table 2 above show that all of the ID1 sequence of pXL3426 (20-mer) is required for the formation of a stable triple helix structure with an oligonucleotide of the type 5'-TT(CTT)$_6$-3'. In particular, the two Py*PuPy portions located at the 5' and 3' ends, and also the central portion, contribute very greatly and cooperatively to the stability of the final structure.

EXAMPLE 5

Influence of the Canonical Triads and of the Number of Noncanonical Triads on the Stability of the Triple Helix The sequence of the oligonucleotide 5'-TT(CTT)$_6$-3' (SEQ ID NO: 2) was modified, and the capacity of these various oligonucleotides (FRB15, FRB16 and FRB17) to form a stable triple helix with the internal ID1 sequence (5'-AA GAA GCA TGC AGA GAA GAA-3'; SEQ ID NO: 1) of the plasmid pXL3426 was tested.

TABLE 3

| Oligo-nucle-otide | Sequence of the oligonucleotide Target ID1 sequence in the plasmid | Number of noncan-onical traids | Capacity (µg plasmid attached per ml of gel) |
|---|---|---|---|
| (CTT)7 | TT CTT CTT CTT CTT CTT CTT (SEQ ID NO: 2) AA GAA GCA TGC AGA GAA GAA (SEQ ID NO: 1) | 6 | 130 |
| FRB15 | TT CTT CTT GCT TCT CTT CTT (SEQ ID NO: 3) AA GAA GCA TGC AGA GAA GAA (SEQ ID NO: 1) | 3 | 189 |
| FRB16 | TT CTT CTT GTT TCT CTT CTT (SEQ ID NO: 4) AA GAA GCA TGC AGA GAA GAA (SEQ ID NO: 1) | 4 | 171 |
| FRB17 | TT CTT CTT CCT TCT CTT CTT (SEQ ID NO: 5) AA GAA GCA TGC AGA GAA GAA (SEQ ID NO: 1) | 3 | 183 |

The results given in Table 3 above show that it is possible to increase the stability of the triple helix structure by modifying the sequence of the oligonucleotide so as to increase the number of T*AT and $^+$C*GC canonical triads, which, at the same time, decreases the number of noncanonical triads in the median internal region N of the triple helix structure.

EXAMPLE 6

Influence of the Noncanonical Triads on the Stability of the Triple Helix Structure The sequence of the plasmid pXL3426 comprising the internal ID1 sequence-(SEQ ID NO: 1) of the FGF1 gene, which is capable of forming a stable triple helix with the oligonucleotide 5'-TT(CTT)$_6$-3' (SEQ ID NO: 2), was modified in order to introduce into the central region N two consecutive identical noncanonical triads of the T*GC type, followed in 5' by a C*AT noncanonical triad (pXL3675). In another experiment, five successive C*AT, T*GC, T*GC, C*AT and T*GC noncanonical triads were introduced (pXL3676). Finally the sequence of the plasmid pXL3426 was modified so as to introduce into the median region two consecutive noncanonical triads of the T*TA type, followed in 5'by a C*TA noncanonical triad (pXL3713).

TABLE 4

| Plasmids | Sequence of the oligonucleotide Target sequence in the plasmid | Capacity (µg plasmid attached per ml of gel) |
| --- | --- | --- |
| pXL3426 | TT CTT CTT CTT CTT CTT CTT (SEQ ID NO: 2) AA GAA GCA TGC AGA GAA GAA (SEQ ID NO: 1) | 112 |
| pXL3675 | CTT CTT CTT CTT CTT CT (SEQ ID NO: 26) GAA GAA GGG AAA GAA GA (SEQ ID NO: 27) | 99 |
| pXL3676 | CTT CTT CTT CTT CTT CT (SEQ ID NO: 26) GAA GAA AGG AGA GAA GA (SEQ ID No. 28) | 78 |
| pXL3713 | CTT CTT CTT CTT CTT CT (SEQ ID NO: 26) GAA GAA GTT TAA GAA GA (SEQ ID NO: 29) | <1 |

The results of purification of the various plasmids, which are given in Table 4 above, show that a stable triple helix structure is formed when the noncanonical central region forms triads of the T*CG, T*GC, C*AT and C*TA type. As shown by the yield of attachment to affinity gel of the plasmids pXL3675 and pXL3676, a stable triple helix is also formed when two consecutive noncanonical T*GC triads are introduced, this being whatever the context, i.e. whether the surrounding triads are canonical or noncanonical in nature. On the other hand, the introduction of a pair of contiguous triads of the T*TA type and of a contiguous C*TA triad leads to complete destabilization of the triple helix structure.

EXAMPLE 7

Constructions of Plasmids Comprising a Cassette Encoding an SeAP, h☐FP, FIX and GAX Gene The genes used in these experiments in order to demonstrate the activity of the compositions of the invention are, for example, the human gene encoding factor F IX (Kurachi et al., Proc. Natl. Acad. Sci. U.S.A. 79(1982)6461), the human gene encoding secreted alkaline phosphatase SeAP (Millan et al., J. Biol. Chem., 261 (1986) 3112), the human gene encoding alpha feto-protein hαFP (Gibbs et al., Biochemistry 26 (1987) 1332), and the human gene encoding GAX (Gorski et al., Mol. Cell. Biol., 13 (1993) 3722). These genes were amplified by PCR using plasmids or cDNA libraries (Clontech), and then cloned downstream of the eukaryotic CMV E/P promoter and upstream of the SV40 late polyA signal sequence, in a PCOR plasmid derived from pXL3296. The gene encoding secreted alkaline phosphatase (SeAP) was introduced into a pCOR plasmid derived from pXL3296 so as to generate the plasmid pXL3402 (FIG. 4). The gene encoding alpha fetoprotein (hxFP) was introduced into a pCOR plasmid derived from pXL3296 so as to generate the plasmid pXL3678 (FIG. 5). The gene encoding GAX was introduced into a pCOR plasmid derived from pXL3296 so as to generate the plasmid pXL3207 (FIG. 6). The gene encoding factor FIX was introduced into a PCOR plasmid derived from pXL3296 so as to generate the plasmid pXL3388 (FIG. 7).

EXAMPLE 8

Use of an Oligonucleotide of the 5'-(CTT)7-3' Type to Generate the Formation of Stable Triple Helix Structures with Various Genes of Interest The interaction of various sequences with the triple helix interaction gel functionalized with the oligonucleotide 5'-TT (CTT)$_6$-3' (SEQ ID NO: 2) was studied by measuring the capacity obtained with plasmids carrying various genes. The genes studied were i) the human gene encoding the factor IX, ii) the gene for secreted alkaline phosphatase SeAP, iii) the human gene for alpha feto-protein (αFP) and iv) the human GAX gene.

TABLE 5

| Genes | Target sequence(s) in the gene | Capacity (µg plasmid attached per ml of gel) |
| --- | --- | --- |
| Factor IX | GAA GAA GCA CGA GAA G (SEQ ID NO: 6) | 71 |
| SEAP | AAA GAA AGC AGG GAA G (SEQ ID NO: 7) GAA GAG GAA GAA G (SEQ ID NO: 8) | 100 |
| hαFP | AAG GAG AAG AAG AA (SEQ ID NO: 9) | 146 |
| hGAX | AA GAT GAG GAA GAA G (SEQ ID NO: 10) | 118 |

The results given in Table 5 above show that it is possible, using an oligonucleotide of the (CTT)$_n$ type, to form stable triple helix structures with a gene of interest, even though this gene does not contain a target sequence of the 5'-(GAA)$_n$-3' type complementary to the oligonucleotide. The existence, in the central portion of the target sequence, of bases involved in triads of the T*CG, C*CG, T*GC and C*AT type is tolerated by the triple helix structure, as is the presence of an isolated T*TA triad (GAX gene).

EXAMPLE 9

Use of a Column Functionalized with an Oligonucleotide of the 5'-(CTT)$_7$-3' Type for Purifying a Plasmid Containing the Internal ID1 Sequence (5'-AA GAA GCA TGC AGA GAA GAA-3'; SEQ ID NO: 1)

The possibility of purifying plasmids carrying a sequence of the 5'-(R)$_n$—(N)$_t$—(R')$_m$-3' type, as described above, using a chromatographic support for affinity by triple helix interaction, functionalized with an oligonucleotide of the 5'-(CTT)$_7$-3' type was studied based on Example 8.

The plasmid pXL3179 (comprising the human FGF1 gene, which carries the sequence 5'-AA GAA GCA TGC AGA GAA GAA-3' SEQ ID NO: 1) was chromatographed on a Sephacryl S-1000 interaction column functionalized with the oligonucleotide 5'-NH$_2$—(CH2)$_6$—(CTT)$_7$-3'. For this, 9.40 mg of plasmid pXL3179 in 60 ml of 50 mM sodium acetate, 2 M NaCl buffer (pH 4.5) were injected, at a flow rate of 30 cm/h, onto a 10 ml affinity column containing the oligonucleotide 5'-NH$_2$—(CH2)$_6$—(CTT)$_7$-3' covalently coupled to Sephacryl S-100 SF as described in Example 3. After washing the column with 5 volumes of the same buffer, the attached plasmid was eluted with 2 column volumes of 100 mM Tris/HCl, 0.5 mM EDTA buffer and quantified by measuring the UV absorbance (260 nm) and by ion exchange chromatography on a GenPak-Fax column (Waters). The *E. coli* genomic DNA content in the initial preparation and in the purified fraction was measured by PCR as described in WO 96/18744. 7.94 mg of plasmid pXL3179 were found in the eluted fraction (elution yield, 84%) and the level of contamination with *E. coli* genomic DNA was decreased from 7.8 to 0.2% with the affinity chromatography described. Similarly, the level of contamination with RNAs was decreased from 43% in the starting plasmid to 0.2% in the purified plasmid.

In various other chromatography experiments carried out on various plasmid pXL3179 preparations chromatographed on a Sephacryl S-1000 affinity column functionalized with the oligonucleotide 5'-NH$_2$—(CH2)$_6$—(CTT)$_7$-3', the genomic DNA content was reduced from 0.2% to 0.007%, from 0.7% to 0.01%, from 7.1% to 0.2%, or from 7.8% to 0.1%.

EXAMPLE 10

Use of an Oligonucleotide of the 5'-CCT TTT CCT CCT T-3' type (SEQ ID NO: 12) to Generate the Formation of Stable Triple Helix Structures with a Gene of Therapeutic Interest, Human VEGFB-167

The interaction of a sequence internal to a gene of therapeutic interest (human VEGFB-167) with a triple helix interaction support functionalized with the oligonucleotide 5'-CCT TTT CCT CCT T-3' (SEQ ID NO: 12) was studied by measuring the capacity obtained with the plasmid pXL3579 carrying the human VEGFB-167 gene (FIG. 8) (Olofsson et al., *J. Biol. Chem.*, 271 (1986) 19310). The plasmid pXL3579, which is represented in FIG. 8, contains the VEGF-B167 gene amplified by PCR from a human heart cDNA library (Clontech), and then cloned downstream of the eukaryotic CMV E/P promoter (–522/+74) and upstream of the SV40 late polyA signal sequence, between the NsiI and XbaI sites of the multiple cloning site of pXL3296.

TABLE 6

| Oligonucleotide | Target sequence in the gene (VEGFB-167 or control) | Capacity (µg plasmid attached per ml of gel) |
|---|---|---|
| CCT TTT CCT CCT T (SEQ ID NO: 12) | GGC AAC GGA GGA A (SEQ ID NO: 13) | 87 |
|  | none (control vector) | <0.5 |
| CCT CCT T (SEQ ID NO: 30) | GGA GGA A (SEQ ID NO: 31) | <0.5 |
|  | none (control vector) | <0.5 |
| TTT TTT TTC CT (SEQ ID NO: 32) | AAA AAA AAG GA (SEQ ID NO: 33) | 15 |
|  | none (control vector) | <0.5 |

The results given in Table 6 above show that it is possible, using an oligonucleotide, such as for example the oligonucleotide 5'-CCT TTT CCT CCT T-3' (SEQ ID NO: 12), which targets a sequence of the 5'-(R)$_n$—(N)$_t$—(R')$_m$-3' type, here the region 5'-GGC AAC GGA GGA A-3(SEQ ID NO: 13) of the human VEGFB-167 gene, to form a stable triple helix structure with a region of a gene of interest. Although, moreover, the human VEGFB-167 gene contains a homopurine sequence 5'-AAA AAA AAG GA-3'(SEQ ID NO: 33) targeted by the oligonucleotide 5'-1TTT TTT TTC CT-3'(SEQ ID NO: 32) (Table 6), the interaction obtained with the oligonucleotide 5'-CCT TTT CCT CCT T-3'(SEQ ID NO: 12) is very greatly superior to the interaction obtained with the homopyrimidine oligonucleotide. Similarly, the internal homopurine sequence 5-GGA GGA A-3' (SEQ ID NO: 31) is not sufficiently long to enable the formation of a stable triple helix with the oligonucleotide 5'-CCT CCT T-3' (SEQ ID NO: 30).

This example therefore clearly shows the advantage of the sequences of the 5'-(R)$_n$—(N)$_t$—(R')$_m$-3' type for forming stable triple helix structures, even in a context in which the double-stranded DNA studied exhibits, moreover, at least one homopurine structure of significant length.

EXAMPLE 11

Use of an Oligonucleotide 5'-T CCT CTC CCT C'-3' (SEQ ID NO: 14) to Generate the Formation of Stable Triple Helix Structures with a Gene of Therapeutic Interest, the Human VEGFB-186

Genetic reorganizations and deletions have been observed during production of human VEGFB-186 within the Exon 6A. Silent single nucleotide mutations have been then introduced by mutageneic and sequential PCR in nucleotides 510 (A/C), 513 (C/T), 516 (A/T), 519 (C/T), 522 (C/T) with reference to the start transcription site. Amino acid sequence of the VEGFB-186 which is comprised between amino acid 170 and 174 remains the same. However, the gene VEGFB-186 so modified (VEGFB-186m) contains a DNA target sequence 5'-A GGA GCG GGA G-3' (SEQ ID NO: 15) according to the present invention, which is capable of forming a stable triple helix interaction with the oligonucleotide 5'-T CCT CTC CCT C-3' (SEQ ID NO: 14). This stable triple helix interaction is used, according to the present invention, to separate the gene VEGFB-186 m from the one which contains genetic reorganizations or deletions within nucleotide sequence of Exon 6A.

Plasmids pXL3601, pXL3977, and pXL3579 are used to demonstrate purification method of the gene VEGFB-186 m according to the present invention. The gene VEGFB-186 is amplified by PCR using a human myocardium cDNA library (Clontech), and cloned downstream of the SV40 late polyA signal, between sites NsiI and XbaI in the cloning multisite of pXL3296 (Example 1.2), thereby generating pXL3601. The plasmid pXL3601 is then modified by sequential and mutageneic PCR to generate pXL3977, wherein the VEGFB-186 contains silent single nucleotide polymorphisms as described herein above.

The interaction of a sequence internal to the gene VEGFB-186 m, i.e., 5'-A GGA GCG GGA G-3' (SEQ ID NO: 15) with a triple helix interaction support functionalized with the oligonucleotide 5-T CCT CTC CCT C-3' (SEQ ID NO: 14) was assessed by measuring the capacity obtained with the plasmid pXL3977 (FIG. 9). The short isoform VEGFB-167, which is spliced in the region of the exon 6A, is also generated during the production of VEGFB-186 m. Plasmid pXL3579 (Example 10) which contains the human VEGFB-167 is thus used as a negative control. Plasmids pXL3977 and pXL3579 only differ by a deletion of at least 11 nucleotides.

TABLE 7

| Oligo-nucleotide | pCOR-VEGF-B186m (pXL3977) (capacity: μg plasmid attached per ml of gel) | PCOR-VEGF-B167 (pXL3579) (μg plasmid attached per ml of gel) | pCOR vide (pXL3296) (μg plasmid attached per ml of gel) |
|---|---|---|---|
| ID n°14 | 234 | 32 | <1.0 |
| ID n°16 | 224 | 0.5-1.0 | <1.0 |

The results given in Table 7 above show that it is possible, using an oligonucleotide, such as for example the oligonucleotide 5'-T CCT CTC CCT C-3' (SEQ ID NO: 14), which targets a sequence of the 5'-$(R)_n$—$(N)_t$—$(R')_m$-3' type, here the region 5'-A GGA GCG GGA G-3' (SEQ ID NO: 15) of the human VEGFB-186 m gene, to form a a stable triple helix structure with a region of a gene of interest. An oligonucleotide having a sequence 5'-TTT CCT CTC CCT C-3' (SEQ ID NO: 16) may also be used for the purification of the VEGFB-186 m gene.

We claim:

1. A process for purifying a double-stranded DNA molecule, comprising contacting said double-stranded DNA molecule with a third DNA strand, said double-stranded DNA molecule comprising at least one target sequence of general formula I:

$$5'\text{-}(R)_n\text{—}(N)_t\text{—}(R')_m\text{-}3' \qquad (I)$$

wherein:
R and R' represent nucleotide sequences composed only of purine bases;
n and m are integers less than 9, and the sum of n+m is greater than 5;
N is a nucleotide sequence comprising both purine bases and pyrimidine bases; and
t is an integer less than 8;
said DNA sequence being capable of interacting with a third DNA strand so as to form a triple helix structure; and purifying the double-stranded DNA molecule.

2. The process according to claim 1, wherein the interaction between the region N and the third DNA strand produces the formation of at most 6 noncanonical triads.

3. The process according to claim 2, wherein the noncanonical triads thus formed are chosen from the T*CG, T*GC, C*AT and C*TA triads.

4. The process according to claim 1, wherein the regions R and R' comprise at least two guanines.

5. The process according to claim 1, wherein the regions R and R' comprise at least two adenines.

6. The process according to claim 1, wherein the regions R and R' form, with the third DNA strand, canonical triads chosen from T*AT and +C*GC.

7. The process according to claim 1, wherein the third DNA strand is of the homopyrimidine type.

8. The process according to claim 7, wherein the third DNA strand comprises a poly-CTT sequence.

9. The process according to claim 1, wherein the third DNA strand is an oligonucleotide.

10. The process according to claim 1, wherein the target sequence naturally present on the DNA molecule is present in the coding sequence of genes of therapeutic or experimental interest.

11. The process according to claim 10, wherein the target DNA sequence comprises SEQ ID NO: 6.

12. The process according to claim 10, wherein the target DNA sequence comprises SEQ ID NO: 7 or SEQ ID NO: 8.

13. The process according to claim 10, wherein the target DNA sequence comprises SEQ ID NO: 9.

14. The process according to claim 10, wherein the target DNA sequence comprises SEQ ID NO: 10.

15. The process according to claim 10, wherein the target DNA sequence comprises SEQ ID NO: 13.

16. The process according to claim 1, wherein the third DNA strand is covalently or noncovalently, stably coupled to a support and comprises the sequence GAGGCTTCTTCT-TCTTCTTCTTCTT (SEQ ID NO: 11).

17. A process for detecting a double-stranded DNA, comprising contacting a solution suspected of containing said double-stranded DNA molecule with a labeled third DNA strand capable of forming, by hybridization, a triple helix with a target sequence of said double-stranded DNA, said target sequence having the following general formula I:

$$5'\text{-}(R)_n\text{—}(N)_t\text{—}(R')_m\text{-}3' \qquad (I)$$

wherein:
R and R' represent nucleotide sequences composed only of purine bases;
n and m are integers less than 9, and the sum of n+m is greater than 5;
N is a nucleotide sequence comprising both purine bases and pyrimidine bases; and
t is an integer less than 8;
and thereby detecting the double-stranded DNA.

* * * * *